(12) United States Patent
Householder et al.

(10) Patent No.: US 12,336,867 B2
(45) Date of Patent: Jun. 24, 2025

(54) BIOPSY SITE MARKERS WITH NON-MIGRATION FEATURES

(71) Applicant: Devicor Medical Products, Inc., Cincinnati, OH (US)

(72) Inventors: Garrett A. Householder, Cincinnati, OH (US); Andrew Nock, Dayton, OH (US); Melody L. Stamper, Batavia, OH (US); Grant Walters, West Chester, OH (US); Brennan Gallagher Mccabe, Cincinnati, OH (US); Jack A. Randall, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 164 days.

(21) Appl. No.: 17/943,380

(22) Filed: Sep. 13, 2022

(65) Prior Publication Data
US 2023/0000588 A1    Jan. 5, 2023

Related U.S. Application Data

(63) Continuation of application No. PCT/US2021/022475, filed on Mar. 16, 2021.
(Continued)

(51) Int. Cl.
*A61B 90/00* (2016.01)
*A61B 17/00* (2006.01)

(52) U.S. Cl.
CPC .... *A61B 90/39* (2016.02); *A61B 2017/00004* (2013.01); *A61B 2017/00898* (2013.01);
(Continued)

(58) Field of Classification Search
CPC .......... A61B 90/39; A61B 2017/00004; A61B 2017/00898; A61B 2090/3908;
(Continued)

(56) References Cited

U.S. PATENT DOCUMENTS

6,083,524 A    7/2000    Sawhney et al.
6,162,241 A    12/2000   Coury et al.
(Continued)

FOREIGN PATENT DOCUMENTS

EP    2512359 A1    10/2012
EP    2737860    *   6/2014
(Continued)

OTHER PUBLICATIONS

Canadian Office Action dated Mar. 22, 2024 for Application No. 3,174,681, 4 pages.
(Continued)

*Primary Examiner* — Alexei Bykhovski
(74) *Attorney, Agent, or Firm* — Frost Brown Todd LLP

(57) ABSTRACT

A biopsy site marker includes a carrier, and a marker element. The marker element includes a primary coil, a first anchor and a second anchor. The primary coil is disposed within the carrier. At least a portion of the first anchor and the second anchor extend outwardly from opposite sides of the carrier. The first anchor and second anchor are configured to move relative to the primary coil to engage tissue at a biopsy site.

16 Claims, 10 Drawing Sheets

Related U.S. Application Data

(60) Provisional application No. 62/990,571, filed on Mar. 17, 2020.

(52) U.S. Cl.
CPC ............... *A61B 2090/3908* (2016.02); *A61B 2090/3925* (2016.02); *A61B 2090/3983* (2016.02); *A61B 2090/3987* (2016.02); *A61B 2090/3991* (2016.02)

(58) Field of Classification Search
CPC .... A61B 2090/3925; A61B 2090/3983; A61B 2090/3987; A61B 2090/3991; A61B 10/0233; A61B 2017/00867; A61B 2090/3912; A61B 2090/3966
See application file for complete search history.

(56) References Cited

U.S. PATENT DOCUMENTS

| | | | |
|---|---|---|---|
| 6,270,464 | B1 | 8/2001 | Fulton, III et al. |
| 6,356,782 | B1 | 3/2002 | Sirimanne et al. |
| 6,605,294 | B2 | 8/2003 | Sawhney |
| 7,651,505 | B2 | 1/2010 | Lubock et al. |
| 8,600,481 | B2 | 12/2013 | Sirimanne et al. |
| 8,634,899 | B2 | 1/2014 | Goosen et al. |
| 8,939,910 | B2 | 1/2015 | Fisher |
| 2005/0119562 | A1 | 6/2005 | Jones et al. |
| 2007/0239016 | A1* | 10/2007 | Fisher ............... A61F 2/02 600/458 |
| 2010/0318115 | A1* | 12/2010 | Chanduszko ...... A61F 2/0105 606/200 |
| 2012/0226146 | A1* | 9/2012 | Schwartz ............ A61B 90/98 359/871 |
| 2014/0018663 | A1 | 1/2014 | Harmer et al. |

FOREIGN PATENT DOCUMENTS

| | | |
|---|---|---|
| JP | 2009-509709 A | 3/2009 |
| WO | 1996/008208 A1 | 3/1996 |
| WO | 2000/024332 A1 | 5/2000 |
| WO | 2000/038579 A2 | 7/2000 |
| WO | 2006/056739 A2 | 6/2006 |
| WO | WO2011075380 * | 6/2011 |
| WO | 2016/073912 A1 | 5/2016 |

OTHER PUBLICATIONS

European Communication dated Jun. 7, 2024 for Application No. 21720034.4, 4 pages.
International Search Report and Written Opinion dated Jul. 20, 2021 for Application No. PCT/US2021/022473, 12 pages.
International Search Report and Written Opinion dated Sep. 13, 2021 for Application No. PCT/US2021/022475, 16 pages.
Japanese Office Action dated Jan. 7, 2025 for Application No. 2022-556096, 27 pages.

* cited by examiner

BIOPSY SITE MARKERS WITH NON-MIGRATION FEATURES

PRIORITY

This application is a continuation of International Application Number PCT/US2021/022475, entitled "Biopsy Site Markers with Non-Migration Features," filed on Mar. 16, 2021, which claims priority to U.S. Provisional Application Ser. No. 62/990,571, entitled "Non-Migrating Biopsy Site Identifiers," filed on Mar. 17, 2020, the disclosures of which are incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MM) or x-ray may be used to locate the biopsy site. In order to assist the relocation of the biopsy site, a marker may be placed at the time of the biopsy.

The use of markers used after breast biopsies to mark the location where the biopsied tissue was removed is described in the following US Patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

Once a marker is placed at a biopsy site, the marker can later be relocated to identify the biopsy site in subsequent follow-up procedures. In some contexts, a placed marker may not completely correspond to the biopsy site when the marker is relocated. For instance, the marker may migrate to another nearby location during the intervening time between the biopsy procedure and subsequent follow up procedures. Migration of the biopsy site marker can cause difficulties when identifying the biopsy site during subsequent follow-up procedures. Accordingly, it may be desirable to incorporate features into a marker to maintain the marker in a fixed position over time.

While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1A:
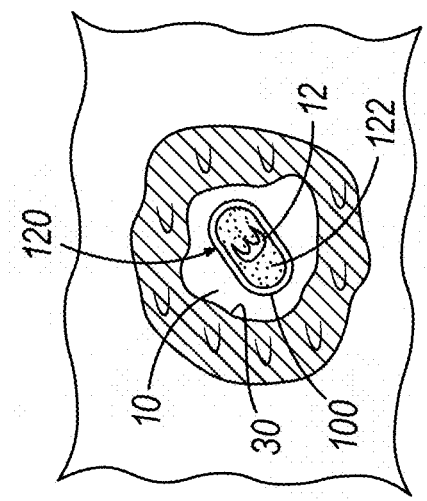
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. Exemplary Marker

Figure 1B:
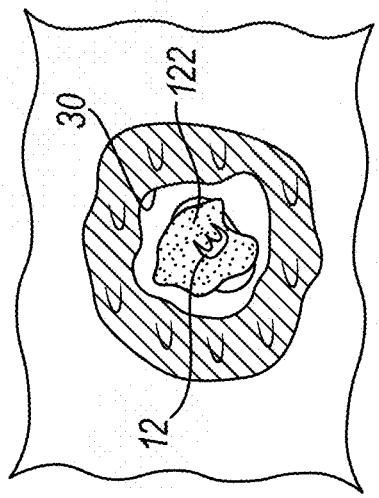
Figure 1C:
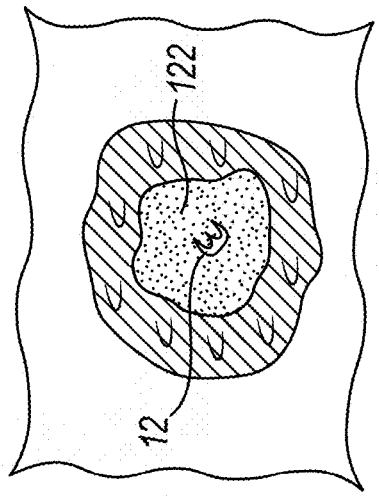

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials.

In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel-based marker material (122) centers marker (100) in the biopsy cavity as it grows. As the hydrogel expands, naturally present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. Exemplary Marker Delivery Device

Figure 2:
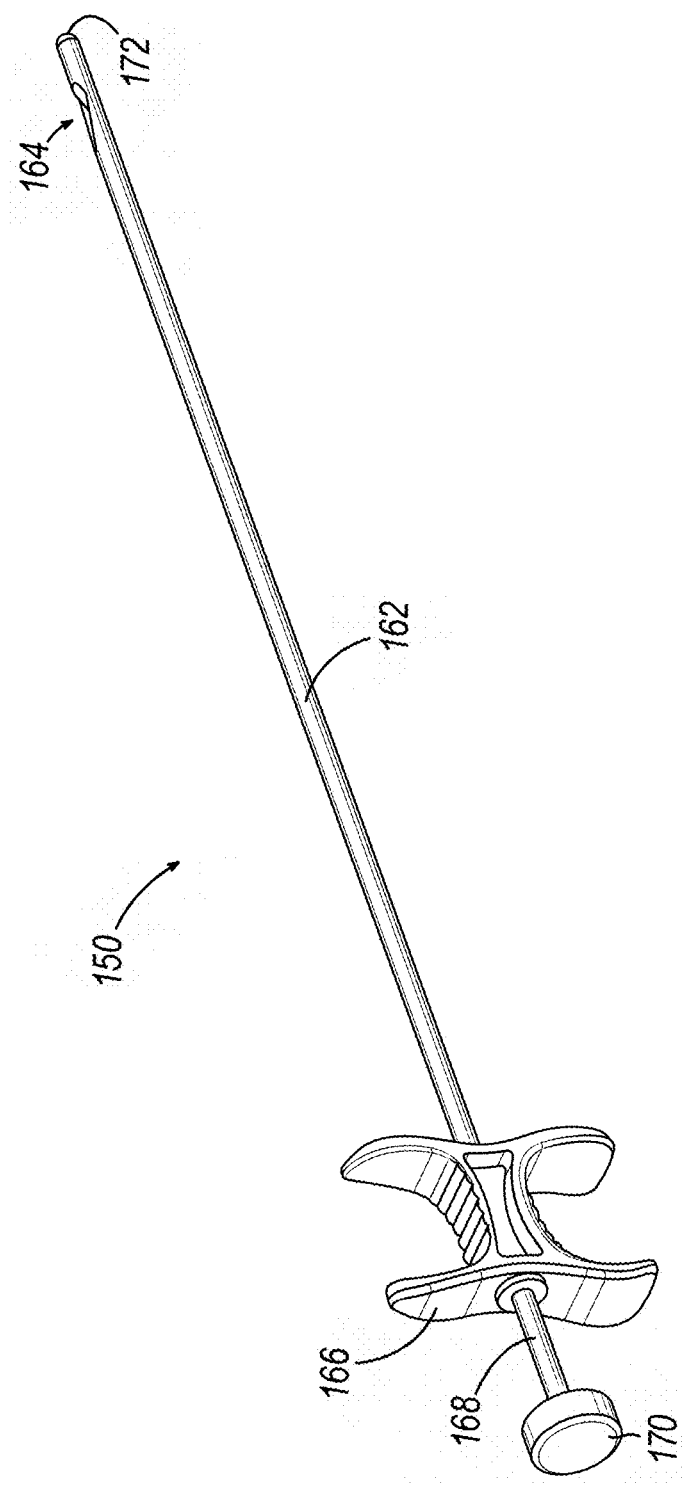
FIG. 2 depicts a perspective view of an exemplary marker delivery device.

In some examples it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through opening (164), yet be relatively flexible in bending. A plunger (170) is coupled at the proximal end of rod (168) for forcing rod (168) distally in cannula (162) to deploy a marker out of cannula (162).

A user may grasp grip (166) with two fingers, and may push on plunger (170) using the thumb on the same hand, so that marker delivery device (160) is operated by a user's single hand. A spring (not shown) or other feature may be provided about rod (168) to bias rod (168) proximally relative to grip (166) and cannula (162).

Figure 3:
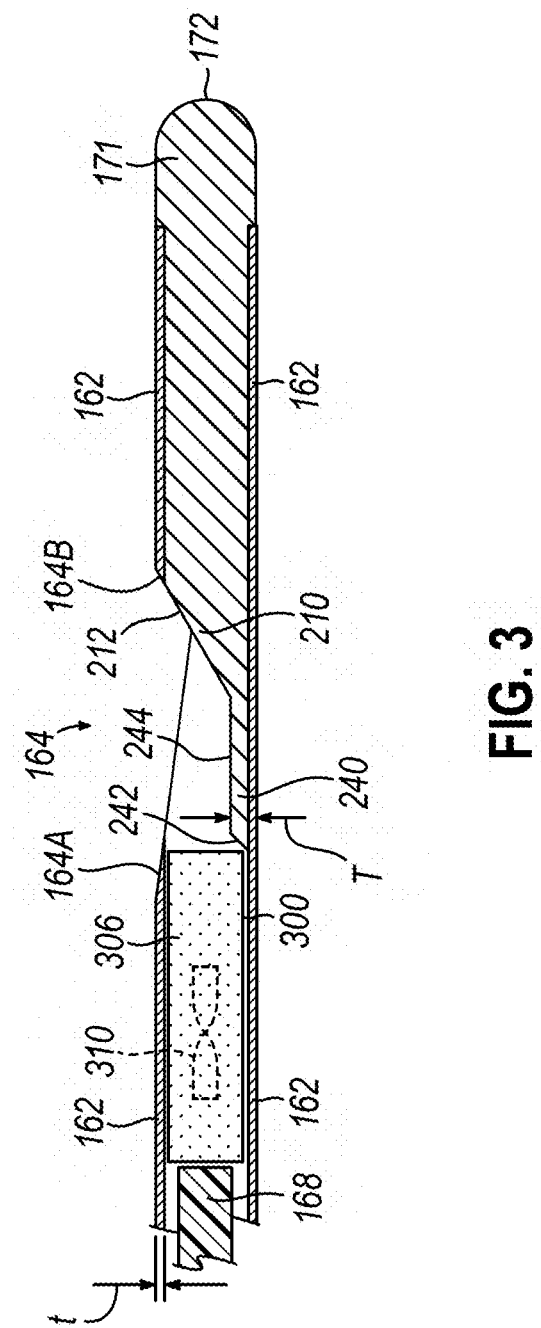
FIG. 3 depicts a side cross-sectional view of the marker delivery device of FIG. 2.

FIG. 3 shows a cross-sectional view of a distal portion of the marker delivery device (160). As can be seen, a biopsy marker (300) similar to marker (100) described above is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin-walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX, and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212), and does not extend proximally of side opening (164), though in other embodiments, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
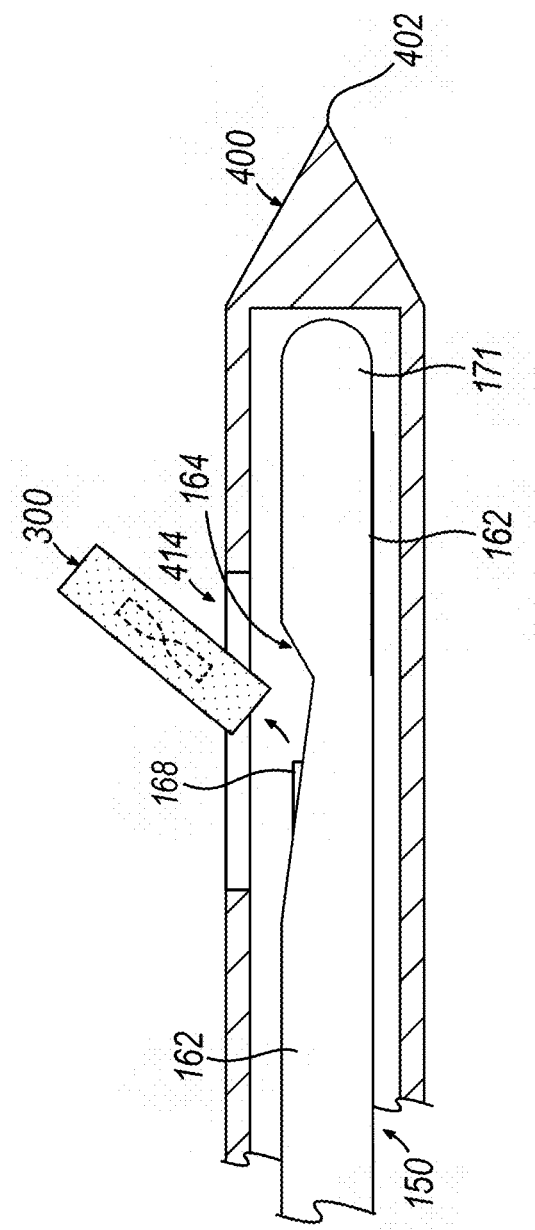
FIG. 4 depicts a cross-sectional view of a marker being deployed from the distal portion of the marker delivery device of FIG. 1 and through a lateral aperture in a biopsy needle to mark a biopsy site.

Referring to FIG. 4, marker delivery device (160) is used to deploy a marker (300) to mark a biopsy location within a patient. In FIG. 4, a cannular biopsy needle (400) is shown having a closed distal end with piercing tip (402) and a lateral tissue receiving aperture (414). Marker delivery device (160) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (160) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (160) is inserted into a proximal opening in needle (400). In FIG. 4, needle (400) and marker delivery device (160) are positioned such that opening (164) of cannula (162) and lateral aperture (414) of needle (400) are substantially aligned axially and circumferentially. Then, with marker delivery device (160) and needle (400) so positioned at the biopsy site, push rod (168) is advanced to deploy marker (300) up ramp surface (212), through opening (164), and then through lateral aperture (414), into the biopsy cavity.

III. Exemplary Biopsy Site Markers for Limited Migration

In some examples it may be desirable to include certain features within a marker similar to marker (100) to reduce a risk of the marker to migrate when placed within tissue. For instance, some markers may be prone to migration after placement of a biopsy site due to movement of tissue in the intervening time between marker placement and subsequent follow-up procedures. As a result, such markers may introduce challenges with identifying the biopsy site during subsequent follow-up procedures. Accordingly, it may be desirable to incorporate features into a marker similar to marker (100) to maintain the marker in a fixed position within tissue over time. Although several examples are described herein that incorporate the features outlined above, it should be understood that various alternative combinations can be used without departing from the basic principles described herein.

A. Exemplary Biopsy Site Marker with Multi-Modal Anchoring

Figure 5B:
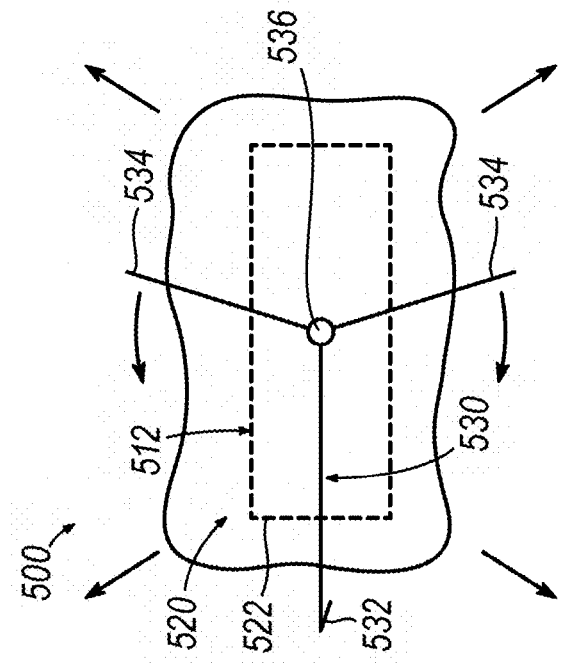
FIG. 5B depicts another top plan view of the marker of FIG. 5A, the carrier of the marker in a partially hydrated state.
Figure 5A:
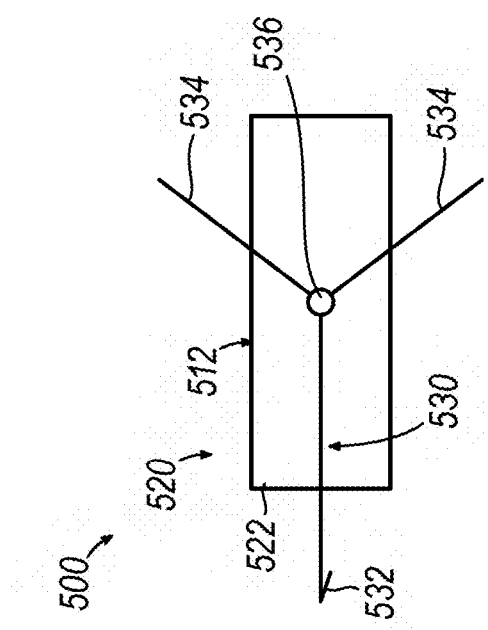
FIG. 5A depicts a top plan view of an exemplary alternative marker for use with the marker delivery device of FIG. 2, a carrier of the marker in a dehydrated state.

FIGS. 5A and 5B show an exemplary marker (500) that is generally configured to anchor to tissue upon delivery at a biopsy site to limit migration of marker (500) relative to an initial placement in tissue. Marker (500) is further generally configured to respond to one or more conditions at a biopsy site to increase anchoring over time, further contributing to limiting the migration of marker (500).

As with marker (100) described above, marker (500) of the present example includes a carrier (520) and a marker element (512). As with carrier (120) described above, carrier (520) of the present example generally includes a bioabsorbable marker material (522). Thus, carrier (520) is generally configured for absorption into a patient after placement of marker (500) within a biopsy cavity such as biopsy cavity (10) described above. Carrier (520) of the present example defines a generally cylindrical shape, although a variety of other shapes may be used. As similarly described above, some examples of carrier (520) may include a plurality of microbubbles to enhance visualization of carrier (520) under ultrasound.

Marker material (522) of the present example comprise a hydrogel or other suitable materials. Hydrogel materials are generally configured to absorb into a patient's tissue over time. Thus, marker material (522) is generally non-permanent. Additionally, hydrogel is generally configured to expand or swell when placed within tissue. As will be described in greater detail below, hydrogel may be dehydrated and/or cured prior to being deployed at a biopsy site or within a biopsy cavity. Once the hydrogel contacts tissue, the hydrogel may absorb moisture from the tissue and expand or swell as the moisture in the hydrogel increases. In some examples, the hydrogel may also be manipulated during dehydration and/or curing to control expansion of the hydrogel in accordance with various expansion profiles (e.g., limit longitudinal expansion, limit transverse expansion, and/or etc.). Although maker material (522) is described herein as being hydrogel, it should be understood that in other examples marker material (522) may comprise other suitable materials or include various combinations of suitable materials with or without hydrogel.

As with marker element (12) described above, marker element (512) of the present example is at least partially disposed within a portion of carrier (520). However unlike marker element (12), one or more portions of marker element (512) is disposed outside of carrier (520). As will be described in greater detail below, this configuration of marker element (512) is generally configured to promote anchoring of marker (500) within tissue.

Marker element (512) of the present example includes a primary anchor (530) (alternatively referred to as a "harpoon"), one or more secondary anchors (534) (alternatively referred to as an "outrigger"), and a coil (536) connecting or joining the primary anchor (530) and the one or more secondary anchors (534). As will be described in greater detail below, anchors (530, 534) are generally configured to engage tissue to anchor marker (500) within tissue.

Primary anchor (530) of the present example is generally configured to provide initial engagement and anchoring with tissue. To promote such engagement, primary anchor (530) includes a barb (532) disposed on a distal end of primary anchor (530). Similar to a fishhook or other structure, barb (532) is configured to penetrate tissue when forced in one direction (e.g., distally), but to catch or stick to tissue when forced in an opposite direction (e.g., proximally). As such, it should be understood that barb (532) may include a sharp distal end and an angled proximally oriented projection from the sharp distal end. Although the present example is shown as including a single barb (532), it should be understood that in other examples, multiple barbs (532) and or proximally oriented projections may be incorporated into primary anchor (530) along the length of primary anchor (530).

Primary anchor (530) extends distally from coil (536). At least a portion of primary anchor (530) extends outside of carrier (520) such that a portion of primary anchor (530) is configured to engage tissue. As will be described in greater detail below, the particular length of extension of primary anchor (530) is generally related to a predetermined expansion of the hydrogel of carrier (520). For instance, the extension of primary anchor (530) is generally of a sufficient length so that barb (532) remains engaged with tissue even after complete expansion of carrier (520) within tissue.

Although the present example is shown as including a single primary anchor (530), multiple primary anchors (530) may be used in other examples. For instance, in some examples two primary anchors (530) may extend distally from coil (536) at an angle relative to a longitudinal axis defined by carrier (520). In other examples, one primary anchor (530) may extend distally as shown, while another primary anchor (530) may extend proximally from coil (536). In yet other examples, multiple primary anchors (530) may extend distally from coil (536) proximally, distally, or both.

One or more secondary anchors (534) extend laterally from coil (536) from the inside of carrier (520) to the outside of carrier (520). One or more secondary anchors (534) are together configured to provide additional anchoring of marker (500) within tissue. As will be described in greater detail below, such anchoring may increase over time once marker (500) is placed within tissue as each secondary anchor (534) is configured to be responsive to expansion of carrier (520).

Each secondary anchor (534) includes an elongate wire rod-shaped construction. Each secondary anchor (534) further extends outwardly from coil (536). The extension of each secondary anchor (534) is shown as being lateral or away from the longitudinal axis defined by carrier (520). Additionally, each secondary anchor (534) is shown as being at an angle relative to the longitudinal axis defined by carrier (520) such that each secondary anchor (534) also extends proximally (or away from the extension of primary anchor (530). In this orientation, each secondary anchor (534) is configured to permit movement of marker (500) in one direction (e.g., distal), yet prevent movement of marker (500) in another direction (e.g., proximal).

Each secondary anchor (534) is configured to have generally spring-like characteristics.

For instance, each secondary anchor (534) may be flexible enough to bend and thereby permit movement in one direction (e.g., distal), yet be rigid enough to prevent movement of marker (500) in the opposite direction (e.g., proximal). Such properties may be facilitated by the particular material of each secondary anchor (534), the dimensions of each secondary anchor (534) (e.g., diameter), or a combination of both.

Marker element (512) of the present example is shown as including two secondary anchors (534) with one secondary anchor (534) protruding from each side of carrier (520). In other examples, marker element (512) may include any suitable number of secondary anchors (534). For instance, in some examples marker element (512) may include a plurality of secondary anchor (534) extending from each side of carrier (520). In other examples, the number of secondary anchors (534) may be asymmetrical with one secondary anchor (534) extending from one side of carrier (520) and multiple secondary anchors (534) extending from another side of carrier (520).

As noted above, coil (536) joins or connects primary anchor (530) and each secondary anchor (536). Coil (536) includes one or more loops of wire material to enhance visualization of marker element (512) under x-ray visualization at a variety of angles relative to the x-ray source and detector. Additionally, the one or more loops of coil (536) may be configured to anchor marker element (512) within carrier (520) to thereby provide a mechanical ground for primary anchor (530) and each secondary anchor (536).

Coil (536) of the present example is integral with primary anchor (530) and each secondary anchor (536). However, in other examples coil (536) may be a separate component with primary anchor (530) and/or each secondary anchor (536) being connected, secured, and/or fastened to coil (536). Regardless, in some examples coil (536) may additionally be configured to provide at least some resiliency to each secondary anchor (536). With the integral construction, coil (536), primary anchor (530), and each secondary anchor (536) include a single common material such as metal. By way of example only, merely exemplary suitable materials for coil (536), primary anchor (530), and each secondary anchor (536) may include biocompatible alloys such as nitinol, stainless steel, titanium, and/or etc.

FIGS. 5A and 5B together show an exemplary use of marker (500). For instance, FIG. 5A shows marker (500) in an initial dehydrated configuration. Such a configuration may correspond to marker (500) being loaded into marker delivery device similar to marker delivery device (150) described above. Such a configuration may also correspond to the condition of marker (500) immediately after deployment at a biopsy site.

In the initial dehydrated configuration, marker (500) may be inserted into a biopsy site using marker delivery device (150) or any other suitable means. During insertion, the sharp tip defined by barb (532) of primary anchor (530) may penetrate into tissue. This penetration sets the adjacent protrusion of barb (532) to set the axial position of marker (500) and limit proximal movement of marker (500) back through the cavity used for deployment of marker (500). Secondary anchors (534) may likewise promote insertion into tissue by bending or otherwise moving in response to distal movement of marker (500) through tissue. Secondary anchors (534) may also limit proximal movement of marker (500) back through the cavity used for deployment of marker (500) due to the proximal orientation of each secondary anchor (534).

After marker (500) is deployed in tissue, marker material (522) may absorb fluid from the surrounding tissue. This absorption will lead to an expansion or swelling of carrier (520) overtime as shown in FIG. 5B. This expansion or swelling may cause corresponding movement of each secondary anchor (534), thereby increasing the angle of each secondary anchor (534) relative to the longitudinal axis of carrier (520). As the angle of each secondary anchor (534) increases, the fixation of marker (500) within the tissue may increase via each secondary anchor (534). Although at least some movement of each secondary anchor (534) may be facilitated by expansion of marker material (522), it should be understood that in some examples at least some movement may be contributed by resiliency in either secondary anchors (534) themselves, or resiliency provided by coil (536).

B. Exemplary Biopsy Site Marker with Bending Member

Figure 6B:
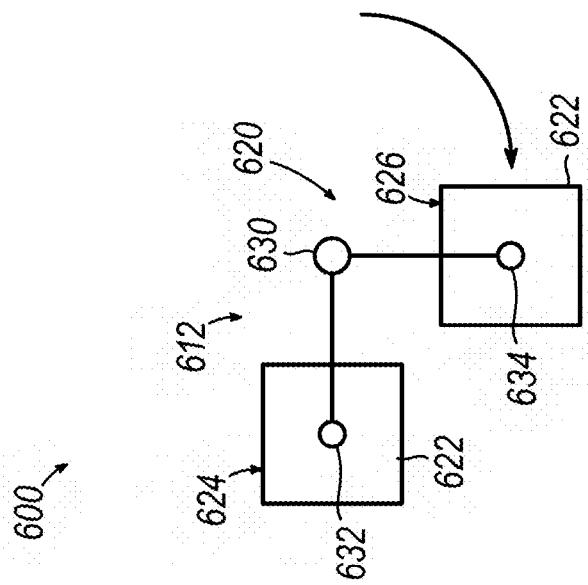
FIG. 6B depicts another top plan view of the marker of FIG. 6A, the marker element of the marker in a bent configuration.
Figure 6A:
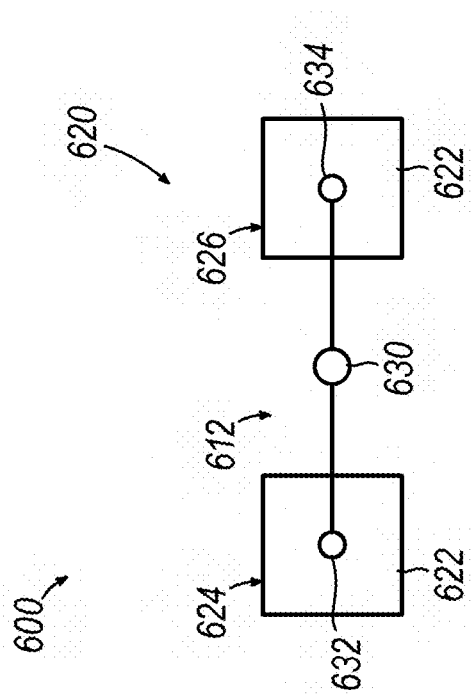
FIG. 6A depicts a top plan view of another exemplary alternative marker for use with the marker delivery device of FIG. 2, a marker element of the marker in a straight configuration.

FIGS. 6A and 6B show an exemplary marker (600) that is generally configured to bend at one or more points to anchor to tissue upon delivery at a biopsy site and limit migration of marker (600) relative to an initial placement in tissue. As with marker (100) described above, marker (600) of the present example includes a carrier (620) and a marker element (612). As with carrier (120) described above, carrier (620) of the present example generally includes a bioabsorbable marker material (622). Thus, carrier (620) is generally configured for absorption into a patient after placement of marker (600) within a biopsy cavity such as biopsy cavity (10) described above. Carrier (620) of the present example defines a generally cylindrical shape, although a variety of other shapes may be used. As similarly described above, some examples of carrier (620) may include a plurality of microbubbles to enhance visualization of carrier (620) under ultrasound.

Marker material (622) of the present example comprise a hydrogel or other suitable materials. Hydrogel materials are generally configured to absorb into a patient's tissue over time. Thus, marker material (622) is generally non-permanent. Additionally, hydrogel is generally configured to expand or swell when placed within tissue. As will be described in greater detail below, hydrogel may be dehydrated and/or cured prior to being deployed at a biopsy site or within a biopsy cavity. Once the hydrogel contacts tissue, the hydrogel may absorb moisture from the tissue and expand or swell as the moisture in the hydrogel increases. In some examples, the hydrogel may also be manipulated during dehydration and/or curing to control expansion of the hydrogel in accordance with various expansion profiles (e.g., limit longitudinal expansion, limit transverse expansion, and/or etc.). Although maker material (622) is described herein as being hydrogel, it should be understood that in other examples marker material (622) may comprise other suitable materials or include various combinations of suitable materials with or without hydrogel.

Unlike carrier (120) described above, carrier (620) is divided into two portions—a primary element (624) and a secondary element (626). As will be described in greater detail below, secondary element (626) is generally configured to move relative to primary element (624) to enhance anchoring in tissue via the combination of primary element (624) and secondary element (626). Both primary element (624) and secondary element (626) are shown in the present example as having a similar cylindrical shape. However, it should be understood that in other examples primary element (624) and secondary element (626) may have dissimilar shapes.

As with marker element (12) described above, marker element (612) of the present example is at least partially disposed within a portion of carrier (620). However unlike marker element (12), one or more portions of marker element (612) is disposed outside of carrier (620). For instance, marker element (612) extends from primary element (624) to secondary element (626), exposing a portion of marker element (612) between primary element (624) and secondary element (626). As will be described in greater detail below, this configuration of marker element (612) is generally configured to promote anchoring of marker (600) within tissue via movement of secondary element (626) relative to primary element (624).

Marker element (612) includes a spring (630) (alternatively referred to as a "resilient member," "drive member," and/or "driver"), a primary coil (632), and a secondary coil (634). Spring (630) disposed between primary coil (632) and secondary coil (634). Although spring (630) is shown in the present example as being centered between primary coil (632) and secondary coil (634), it should be understood that in some examples spring (630) may be disposed off-center relative to primary coil (632) and secondary coil (634).

Regardless of the particular position of spring (630), spring (630) as being positioned outside of both primary element (624) and secondary element (626) of carrier (620). This configuration is generally desirable to permit movement of secondary element (626) relative to primary element (624) about an axis defined by spring (630). Thus, spring (630) is generally configured to drive movement of secondary element (626) and/or primary element (624).

Spring (630) may take a variety of forms suitable for driving movement of secondary element (626) relative to primary element (624). In the present example, spring (630) is shown as a coil or torsion spring. Such a configuration may also be desirable to enhance the visibility of marker element (612) under x-ray by including one or more overlapping coils. However, other suitable configurations may be used. For instance, in some examples spring (630) may include a shape memory material such as nitinol. Spring (630) may then transition from a first relatively straight shape to a second bent shape in response to a temperature increase from surrounding tissue.

Primary coil (632) and secondary coil (634) are disposed on opposing ends of marker element (612). Primary coil (632) is disposed within primary element (624) of carrier (620). Meanwhile, secondary coil (634) is disposed within secondary element (626) of carrier (620). Both coils (632, 634) define a distinctive geometric pattern that may be visible under x-ray and/or ultrasound. For instance, in some examples, coils (632, 634) may include one or more loops of wire material to enhance visualization of marker element (612) under x-ray visualization at a variety of angles relative to the x-ray source and detector. Additionally, the one or more loops of each coil (632, 634) may be configured to anchor marker element (612) within primary element (624)/secondary element (626) of carrier (620) to thereby provide a mechanical ground for marker element (612). In other examples, coils (632, 634) may be of a ribbon or sheet configuration bent at one or more points to provide enhanced visualization under x-ray and/or ultrasound. In any of the above-described configurations for each coil (632, 634), such coils (632, 634) may include one or more openings and/or bores to further enhance visualization. Furthermore, each coil (632, 634) does not necessarily be of identical configurations. Indeed, in some examples it may be desirable to have at least some variation between the configuration of each coil (632, 634) to more readily identify a particular end of marker (600).

Each coil (632, 634) of the present example is integral with the rest of marker element (612). Such a configuration may be desirable to promote ease of manufacturing by, for example, having to bend only a single wire. However, in other examples each coil (632, 634) may be a separate component with other portions of marker element (612) being connected, secured, and/or fastened to each coil (632, 634). With the integral construction, marker element (612) may include a single common material such as metal. By way of example only, merely exemplary suitable materials for each coil (632, 634) and other components of marker element (612) may include biocompatible alloys such as nitinol, stainless steel, titanium, and/or etc.

FIGS. 6A and 6B together show an exemplary use of marker (600). For instance, FIG. 6A shows marker (600) in an initial straight configuration. Such a configuration may correspond to marker (600) being loaded into a marker delivery device similar to marker delivery device (150) described above. While marker (600) is in the straight configuration, marker (600) is generally configured for deployment at a biopsy site using the marker delivery device.

Once marker (600) is deployed at a biopsy site, marker (600) is configured to automatically transition to a bent configuration as shown in FIG. 6B. As can be seen, spring (630) is configured to drive movement of secondary element (626) relative to primary element (624) about an axis defined by spring (630). This transition results in marker (600) being of a more irregular shape and thus more likely to anchor within tissue at a biopsy site. In the present example, a rotation of approximately 90° is shown. However, it should be understood that in other examples various other rotations may be used. By way of example only, one range of suitable rotation angles may include approximately 70° to approximately 100°.

As noted above, spring (630) may be configured to drive movement of secondary element (626) in a variety of ways. In the present example, such movement is accomplished by spring (630) being resiliently biased to rotate secondary element (626) from the position shown in FIG. 6A to the position shown in FIG. 6B. In other examples, spring (630) may include a shape memory alloy. Such an alloy may be sensitive to the temperature of the surrounding tissue and may therefore drive movement of secondary element (626) slowly over time as spring (630) warms from ambient temperature to the temperature of tissue. Such a configuration may be desirable to promote movement of secondary element (626) that is at least partially contemporaneous with expansion and/or swelling of carrier (620).

C. Exemplary Biopsy Site Marker with Plurality of Anchoring Elements

Figure 7B:
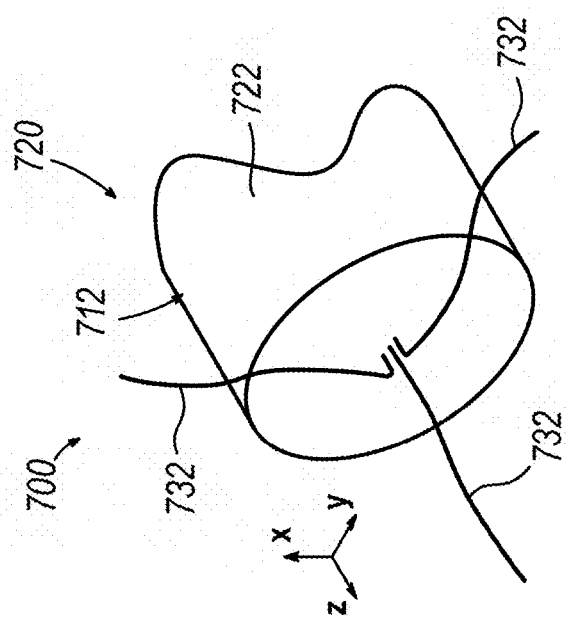
FIG. 7B depicts a partial perspective view of the marker of FIG. 7A.
Figure 7A:
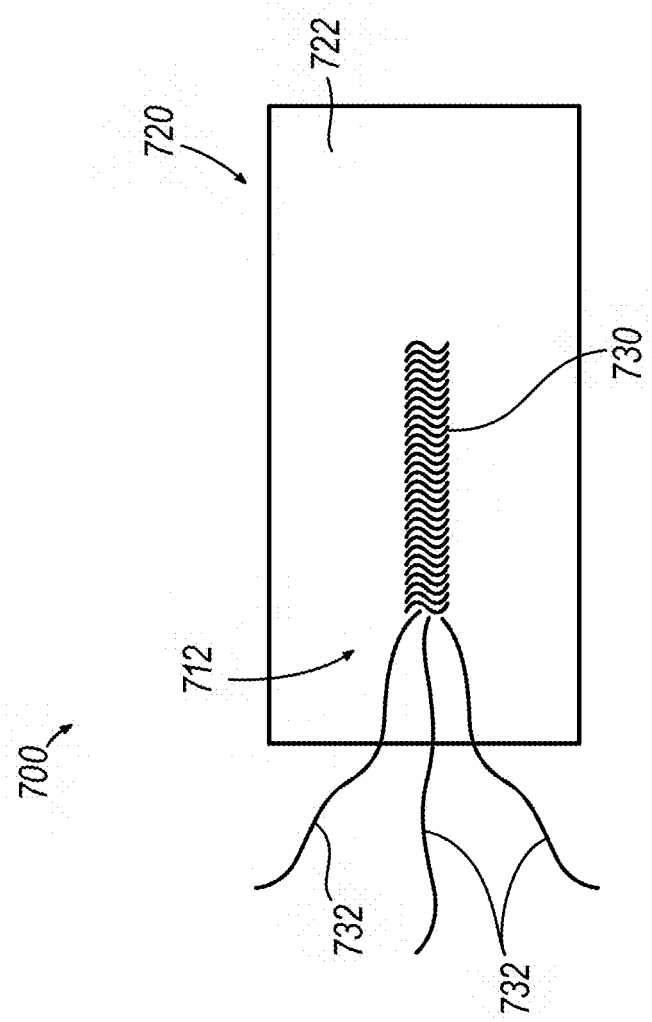
FIG. 7A depicts a top plan view of yet another exemplary alternative marker for use with the marker delivery device of FIG. 2.

FIGS. 7A and 7B show an exemplary marker (700) that is generally configured to anchor to tissue using anchors oriented across multiple planes to limit migration of marker (700) relative to an initial placement in tissue. As with marker (100) described above, marker (700) of the present example includes a carrier (720) and a marker element (712). As with carrier (120) described above, carrier (720) of the present example generally includes a bioabsorbable marker material (722). Thus, carrier (720) is generally configured for absorption into a patient after placement of marker (700) within a biopsy cavity such as biopsy cavity (10) described above. Carrier (720) of the present example defines a generally cylindrical shape, although a variety of other shapes may be used. As similarly described above, some examples of carrier (720) may include a plurality of microbubbles to enhance visualization of carrier (720) under ultrasound.

Marker material (722) of the present example comprise a hydrogel or other suitable materials. Hydrogel materials are generally configured to absorb into a patient's tissue over time. Thus, marker material (722) is generally non-permanent. Additionally, hydrogel is generally configured to expand or swell when placed within tissue. As will be described in greater detail below, hydrogel may be dehydrated and/or cured prior to being deployed at a biopsy site or within a biopsy cavity. Once the hydrogel contacts tissue, the hydrogel may absorb moisture from the tissue and expand or swell as the moisture in the hydrogel increases. In some examples, the hydrogel may also be manipulated during dehydration and/or curing to control expansion of the hydrogel in accordance with various expansion profiles (e.g., limit longitudinal expansion, limit transverse expansion, and/or etc.). Although maker material (722) is described herein as being hydrogel, it should be understood that in other examples marker material (722) may comprise other suitable materials or include various combinations of suitable materials with or without hydrogel.

Marker element (712) includes a braded portion (730) and a plurality of anchor portions (732) (alternatively referred to as "outriggers") extending distally from braided portion (730). In the present example, braided portion (730) is disposed entirely within carrier (720). In other examples, at least a portion of braided portion (730) may extend outside of carrier (720). Braided portion (730) is defined by a plurality of wires braided together in a repeating pattern. Various suitable repeating patterns may be used. Generally, a suitable repeating pattern may be configured to provide a distinctive pattern to enhance visualization under x-ray and/or ultrasound visualization.

Anchor portions (732) extend distally from braided portion (730). In the present example, braided portion (730) includes three wires with anchor portions (732) being formed by three corresponding unbraided wires. Alternatively, in other examples, any suitable number of wires may be used such as two, four, five, or six. Each anchor portion (732) is configured to project outwardly from a distal end of braided portion (730) at a different angle from each other anchor portion (732) to cross multiple different planes. In this configuration, each anchor portion (732) is configured to engage tissue across multiple planes rather than across a single plane.

FIGS. 7A and 7B show an exemplary use of marker (700). For instance, FIG. 7A shows marker (700) in a configuration that in some examples may correspond to the configuration after deployment at a biopsy site using a marker delivery device similar to marker delivery device (150) described above. In this position, anchor portions (732) are generally more compacted or closer together than when in a fully anchored configuration. Although anchor portions (732) are shown as still having some space between each other, it should be understood that in other uses anchor portions (732) may be placed closer together for the purpose of deployment. For instance, in some uses, anchor portions (732) may be pressed together to form a generally straight distal projection. This configuration may be desirable to facilitate smoother deployment using a marker delivery device similar to marker delivery device (150) described above. In other uses, such a straight configuration of anchor portions (732) may be further facilitated by braiding anchor portions (732) in a pattern similar to the pattern of braided portion (730). In such a configuration, such braiding of anchor portions (732) may be relatively loose to promote subsequent spreading of anchor portions (732) relative to each other.

After deployment, anchor portions (732) spread in multiple different directions as shown in FIG. 7B. As a result of this spread, each anchor portion (732) intermeshes with tissue at a biopsy site across multiple different planes. As a result, anchor portions (732) are together configured to anchor marker (700) within tissue across multiple directions (e.g., laterally and longitudinally).

D. Exemplary Biopsy Site Marker with Multi-Planar Anchoring Elements

Figure 8:
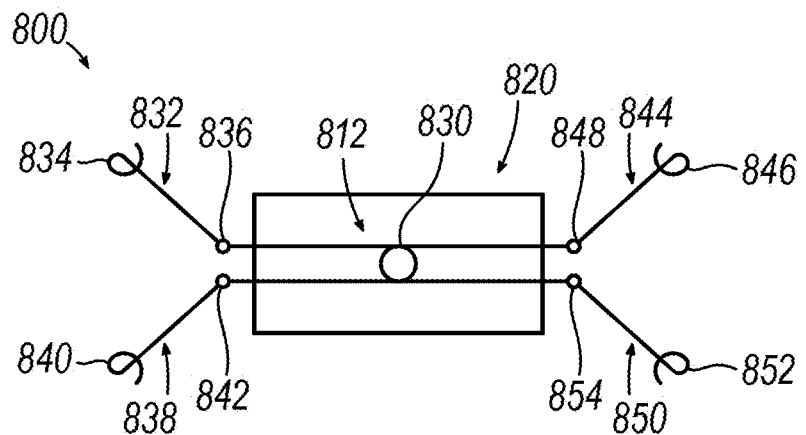
FIG. 8 depicts a top plan view of still another exemplary alternative marker for use with the marker delivery device of FIG. 2.
Figure 9:
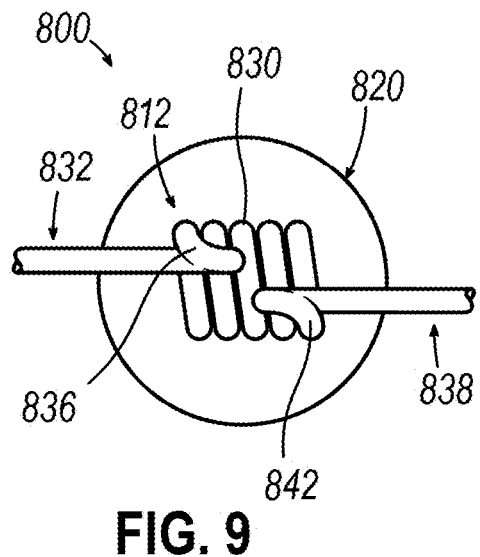
FIG. 9 depicts a front elevational view of the marker of FIG. 8.

FIGS. 8 and 9 show an exemplary marker (800) that is generally configured to anchor to tissue using anchors aligned along multiple planes to limit migration of marker (800) relative to an initial placement in tissue. As with marker (100) described above, marker (800) of the present example includes a carrier (820) and a marker element (812). As with carrier (120) described above, carrier (820) of the present example generally includes a bioabsorbable marker material (822). Thus, carrier (820) is generally configured for absorption into a patient after placement of marker (800) within a biopsy cavity such as biopsy cavity (10) described above. Carrier (820) of the present example defines a generally cylindrical shape, although a variety of other shapes may be used. As similarly described above, some examples of carrier (820) may include a plurality of microbubbles to enhance visualization of carrier (820) under ultrasound.

Marker material (822) of the present example comprise a hydrogel or other suitable materials. Hydrogel materials are generally configured to absorb into a patient's tissue over time. Thus, marker material (822) is generally non-permanent. Additionally, hydrogel is generally configured to expand or swell when placed within tissue. As will be described in greater detail below, hydrogel may be dehydrated and/or cured prior to being deployed at a biopsy site or within a biopsy cavity. Once the hydrogel contacts tissue, the hydrogel may absorb moisture from the tissue and expand or swell as the moisture in the hydrogel increases. In some examples, the hydrogel may also be manipulated during dehydration and/or curing to control expansion of the hydrogel in accordance with various expansion profiles (e.g., limit longitudinal expansion, limit transverse expansion, and/or etc.). Although maker material (822) is described herein as being hydrogel, it should be understood that in other examples marker material (822) may comprise other suitable materials or include various combinations of suitable materials with or without hydrogel.

Marker element (812) includes a primary coil (830) and a plurality of anchors (832, 838, 844, 850) (alternatively referred to as "outriggers") extending outwardly from primary coil (830). In the present example, primary coil (830) is disposed entirely within carrier (820). Primary coil (830) is defined by one or more wire coils. Generally, the combination of the one or more wire coils forming primary coil (830) are configured to provide a distinctive pattern to enhance visualization under x-ray and/or ultrasound visualization. Although primary coil (830) is shown as having a particular orientation within carrier (820) in the present example, it should be understood that primary coil (830) may have a variety of alternative orientations in other examples.

Each anchor (832, 838, 844, 850) extends proximally or distally away from primary coil (830) to protrude from carrier (820). Each anchor (832, 838, 844, 850) includes a corresponding secondary coil (834, 840, 846, 852) and spring (836, 842, 848, 854). Each secondary coil (834, 840, 846, 852) is generally configured as one or more wire loops and is configured to promote tissue in-growth to provide enhanced anchoring of marker (800). Each spring (836, 842, 848, 854) is positioned along a length of each anchor (832, 838, 844, 850) between primary coil (830) and a respective secondary coil (834, 840, 846, 852). As will be described in greater detail below, each spring (836, 842, 848, 854) is configured to bias a respective secondary coil (834, 840, 846, 852) outwardly and into tissue. As such, each spring (836, 842, 848, 854) is positioned along the length of each anchor (832, 838, 844, 850) outside of carrier (820). Although anchors (832, 838, 844, 850) of the present example are shown as being substantially similar to each other, it should be understood that in other examples, anchors (832, 838, 844, 850) may have variation in structure. For instance, in some examples, one or more anchors (832, 838, 844, 850) may include multiple springs, multiple coils, and/or different geometric profiles. Additionally, in some examples, anchors (832, 838, 844, 850) may be of varying lengths with one anchor (832, 838, 844, 850) being longer or shorter than one or more other anchors (832, 838, 844, 850). Various suitable combinations of such features will be apparent to those of ordinary skill in the art in view of the teachings herein.

The present example includes a first anchor (832) and a second anchor (838) extending distally from carrier (820) and a third anchor (844) and a fourth anchor (850) extending proximally from carrier (820). As best shown in FIG. 9, first anchor (832) and second anchor (838) are laterally offset relative to each other. Similarly, third anchor (844) and fourth anchor (850) are also laterally offset relative to each other. In some instances, such a lateral offset may be undesirable due to an asymmetrical anchoring profile. For instance, the lateral offset may promote rolling or some movement of the cylindrical shape of marker (800). However, in the present example, anchors (832, 838, 844, 850) are positioned balance any asymmetry. For instance, first anchor (832) and third anchor (844) may be aligned along a common plane. Similarly, second anchor (838) and fourth anchor (850) may be aligned another common plane offset from the common plane of first anchor (832) and third anchor (844). As a result, marker (800) may have a more balanced anchoring profile with enhanced anchoring provided by the number of anchors (832, 838, 844, 850).

In an exemplary use, marker (800) may initially be disposed in a tubular structure similar to outer cannula (162) of marker delivery device (150) for deployment at a biopsy site. To facilitate confinement within the tubular structure, anchors (832, 838, 844, 850) may bend about springs (836, 842, 848, 854) to conform to the inner diameter of the tubular structure.

During deployment of marker (800), marker (800) may be ejected from the tubular structure as similarly described above with respect to marker delivery device (150). Once marker (800) is released from the tubular structure, the resilient bias of springs (836, 842, 848, 854) may cause anchors (832, 838, 844, 850) to expand. As a result, each secondary coil (834, 840, 846, 852) of each anchor (832, 838, 844, 850) may be forced into adjacent tissue to anchor marker (800) at the biopsy site. Overtime, some tissue in-growth may occur with respect to each secondary coil (834, 840, 846, 852) further increasing anchoring of marker (800) over time.

Figure 10:
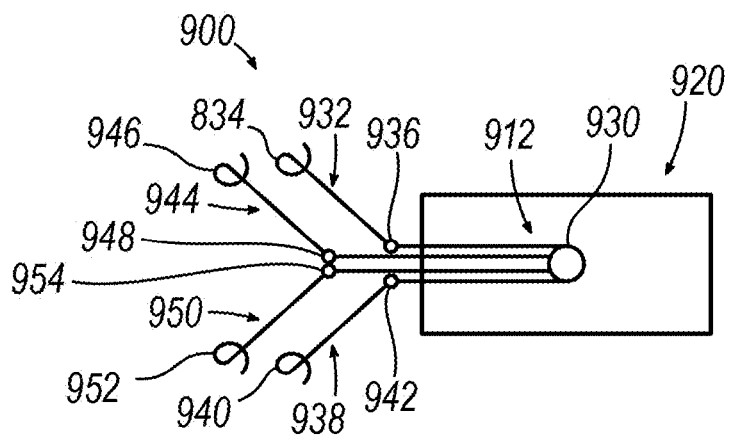
FIG. 10 depicts a top plan view of still another exemplary alternative marker for use with the marker delivery device of FIG. 2.

FIG. 10 shows an exemplary marker (900) that is substantially similar to marker (800) described above. For instance, like with marker (800), marker (900) of the present example includes a carrier (920) and a marker element (912). Carrier (920) of the present example is substantially similar to carrier (820) described above. For instance, carrier (920) is generally configured for absorption into a patent after placement of marker (900) within a biopsy cavity. Similarly, carrier (920) may include a hydrogel or other suitable material configured to expand upon hydration and absorb into a patient's tissue over time.

Marker element (912) is substantially similar to marker element (812) described above. For instance, like with marker element (812), marker element (912) of the present example includes a primary coil (930) with a plurality of anchors (932, 938, 944, 950) extending away from primary coil. Likewise, each anchor (932, 938, 944, 950) includes a secondary coil (934, 940, 946, 952) and a spring (936, 942, 948, 950), with spring (936, 942, 948, 950) being disposed between primary coil (930) and secondary coil (934, 340, 946, 952). As with springs (836, 842, 848, 850) described above, springs (936, 942, 948, 950) of the present example are disposed outside of carrier (920) and are resiliently biased to promote engagement of each secondary coil (934, 940, 946, 952) with tissue.

Unlike anchors (832, 838, 844, 850) described above, anchors (932, 938, 944, 950) of the present example all extend distally away from primary coil (930). In other words, each anchor (932, 938, 944, 950) extends in the same direction relative to the other anchors (932, 938, 944, 950). To accommodate such a relationship, the present example includes anchors (932, 938, 944, 950). For instance, in the present example the inside anchors (944, 950) have a longer length relative to the outside anchors (932, 938) to provide adequate clearance between all anchors (932, 938, 944, 950). Although certain specific lengths for anchors (932, 938, 944, 950) are shown in the present example, in other examples, various alternative lengths may be used. Alternatively, the orientation of each anchor (932, 938, 944, 950) may be modified to provide clearance between anchors (932, 938, 944, 950) rather than having varying length.

Although not shown, it should be understood that anchors (932, 938, 944, 950) of the present example may be laterally offset relative to other anchors (932, 938, 944, 950) as similarly described above with respect to anchors (832, 838, 844, 850). For instance, in some examples an outside anchor (932, 938) may be laterally aligned with an adjacent inside anchor (944, 950) such that the outer anchor (932, 938) and adjacent inside anchor (944, 950) extend along a common plane. Meanwhile, outside anchors (944, 950) may be laterally offset relative to each other. As similarly described above with respect to anchors (832, 838, 844, 850), such a lateral offset may be desirable to provide multiple anchoring points oriented along two or more separate planes.

In an exemplary use, marker (900) may be used similarly as described above with respect to marker (800). For instance, marker (900) may initially be disposed in a tubular structure similar to outer cannula (162) of marker delivery device (150) for deployment at a biopsy site. To facilitate confinement within the tubular structure, anchors (932, 938, 944, 950) may bend about springs (936, 942, 948, 954) to conform to the inner diameter of the tubular structure.

During deployment of marker (900), marker (900) may be ejected from the tubular structure as similarly described above with respect to marker delivery device (150). Once marker (900) is released from the tubular structure, the resilient bias of springs (936, 942, 948, 954) may cause anchors (932, 938, 944, 950) to expand. As a result, each secondary coil (934, 940, 946, 952) of each anchor (932, 938, 944, 950) may be forced into adjacent tissue to anchor marker (900) at the biopsy site. Overtime, some tissue in-growth may occur with respect to each secondary coil (934, 940, 946, 952) further increasing anchoring of marker (900) over time.

E. Exemplary Biopsy Site Marker with Nitinol Tube

Figure 11:
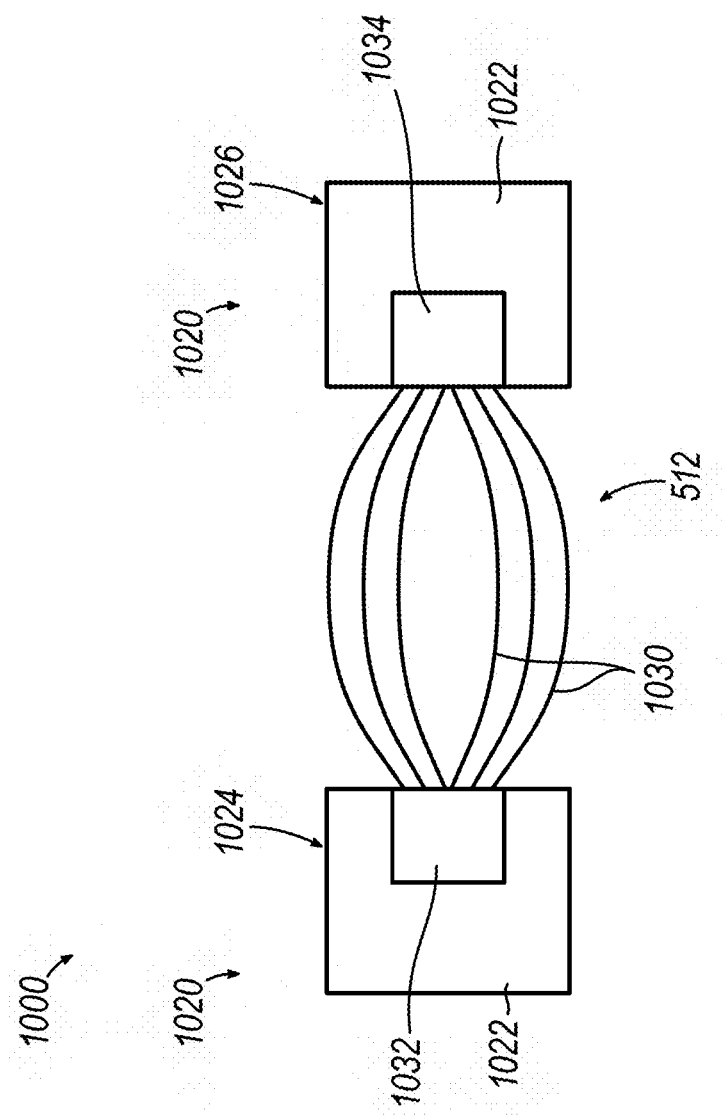
FIG. 11 depicts a top plan view of still another exemplary alternative marker for use with the marker delivery device of FIG. 2.

FIG. 11 shows an exemplary marker (1000) that is generally configured to automatically change shape upon delivery at a biopsy site and limit migration of marker (1000) relative to an initial placement in tissue. As with marker (100) described above, marker (1000) of the present example includes a carrier (1020) and a marker element (1012). As with carrier (120) described above, carrier (1020) of the present example generally includes a bioabsorbable marker material (1022). Thus, carrier (1020) is generally configured for absorption into a patient after placement of marker (1000) within a biopsy cavity such as biopsy cavity (10) described above. Carrier (1020) of the present example defines a generally cylindrical shape, although a variety of other shapes may be used. As similarly described above, some examples of carrier (1020) may include a plurality of microbubbles to enhance visualization of carrier (1020) under ultrasound.

Marker material (1022) of the present example comprise a hydrogel or other suitable materials. Hydrogel materials are generally configured to absorb into a patient's tissue over time. Thus, marker material (1022) is generally non-permanent. Additionally, hydrogel is generally configured to expand or swell when placed within tissue. As will be described in greater detail below, hydrogel may be dehydrated and/or cured prior to being deployed at a biopsy site or within a biopsy cavity. Once the hydrogel contacts tissue, the hydrogel may absorb moisture from the tissue and expand or swell as the moisture in the hydrogel increases. In some examples, the hydrogel may also be manipulated during dehydration and/or curing to control expansion of the hydrogel in accordance with various expansion profiles (e.g., limit longitudinal expansion, limit transverse expansion, and/or etc.). Although maker material (1022) is described herein as being hydrogel, it should be understood that in other examples marker material (1022) may comprise other suitable materials or include various combinations of suitable materials with or without hydrogel.

Unlike carrier (120) described above, carrier (1020) is divided into two portions—a distal element (1024) and a proximal element (1026). As will be described in greater detail below, distal element (1024) and proximal element (1026) are generally spaced from each other by a predetermined distance to permit movement of a portion of marker (1000) relative to distal element (1024) and proximal element (1026). Thus, distal element (1024) and proximal element (1026) together form a generally cylindrical shape, with the cylindrical shape being interrupted by the space between distal element (1024) and proximal element (1026). Both distal element (1024) and proximal element (1026) are shown in the present example as having a similar cylindrical shape. However, it should be understood that in other examples distal element (1024) and proximal element (1026) may have dissimilar shapes.

As with marker element (12) described above, marker element (1012) of the present example is at least partially disposed within a portion of carrier (1020). However unlike marker element (12), one or more portions of marker element (1012) is disposed outside of carrier (1020). For instance, marker element (1012) extends from distal element (1024) to proximal element (1026), exposing a portion of marker element (1012) between distal element (1024) and proximal element (1026). As will be described in greater detail below, this configuration of marker element (1012) is generally configured to promote anchoring of marker (1000) within tissue via movement of one or more of marker element (1012), distal element (1026), and/or proximal element (1024).

Marker element (1012) includes an anchor tube (1030) (alternatively referred to as a "tube," "expansion member," and/or "cross member"), a distal connector (1032), and a proximal connector (1034). Anchor tube (1030) is disposed between distal connector (1032) and proximal connector (1034). Anchor tube (1030) of the present example comprises a plurality of nitinol wires oriented relative to each other to form a tubular structure. As will be discussed in greater detail below, this configuration of anchor tube (1030) is configured to permit expansion of anchor tube (1030) in response to heat from surrounding tissue so that the wires forming anchor tube (1030) engage the surrounding tissue, thereby anchoring marker (1000). Although anchor tube (1030) is formed of a plurality of wires in the present example, it should be understood that in other examples anchor tube (1030) may take on a variety of forms using a variety of materials. For instance, in some examples anchor tube (1030) may be of a tubular sheet material with holes and/or slots extending through the sheet. In such examples, anchor tube (1030) may include nitinol, other biocompatible shape-memory alloys, or biocompatible non-shape-memory alloys.

Distal connector (1032) is disposed on one end of anchor tube (1030) with proximal connector (1034) being disposed on the other end of anchor tube (1030). Each connector (1032, 1034) is at least partially disposed within an element (1024, 1026) of carrier (1020). Thus, each connector (1032, 1034) provides a mechanical ground between anchor tube (1030) and each element (1024, 1026) of carrier (1020). Additionally, each connector (1032, 1034) may be configured to enhance visualization of marker (1000) under ultrasound. For instance, in some examples, each connector (1032, 1034) may include one or more wire coils configured to provide a distinctive pattern under x-ray and/or ultrasonic visualization. In other examples, each connection (1032, 1034) may include a ribbon or sheet material bent or twisted at several locations to provide a distinctive pattern under x-ray and/or ultrasonic visualization.

In some examples, each connector (1032, 1034) may be integral with anchor tube (1030). Thus, in such examples, each connector (1032, 1034) and anchor tube (1030) may comprise the same material as anchor tube (1030). In other examples, each connector (1032, 1034) may comprise a different material relative to anchor tube (1030). In such examples, each connector (1032, 1034) may be integral with anchor tube (1030) using overmolding, forging or other similar processes. Alternatively, each connector (1032, 1034) may be separate from anchor tube (1030) and connected thereto using one or more fasteners, adhesives, and/or other suitable mechanical couplings.

In an exemplary use, marker (1000) may be in an initial configuration with anchor tube (1030) in a generally tubular configuration similar to the configuration shown in FIG. 11. Such a configuration may correspond to marker (1000) being loaded into a marker delivery device similar to marker delivery device (150) described above. While marker (1000) is in the initial configuration, marker (1000) is generally configured for deployment at a biopsy site using the marker delivery device.

Once marker (1000) is deployed at a biopsy site, marker (1000) is configured to automatically transition to an expanded configuration. During this transition, anchor tube (1030) gradually absorbs heat from surrounding tissue. This heat absorption activates the shape-memory properties of anchor tube (1030). In the present example, each wire making up anchor tube (1030) may be configured with a curved pattern larger than the radius defined by carrier (1020) upon activation of the shape-memory property. As a result, anchor tube (1030) will expand upon activation of the shape-memory property, with each wire forming anchor tube (1030) engaging the surrounding tissue with increasing force. Once the expansion is complete, anchor tube (1030) may be configured to anchor marker (1000) within tissue.

Figure 13:
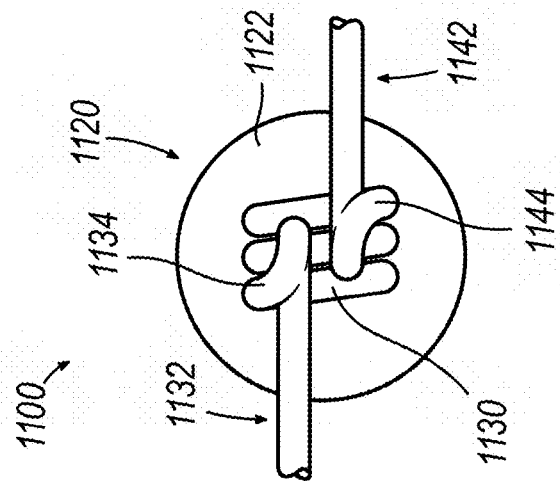
FIG. 13 depicts a front elevational view of the marker of FIG. 12.
Figure 12:
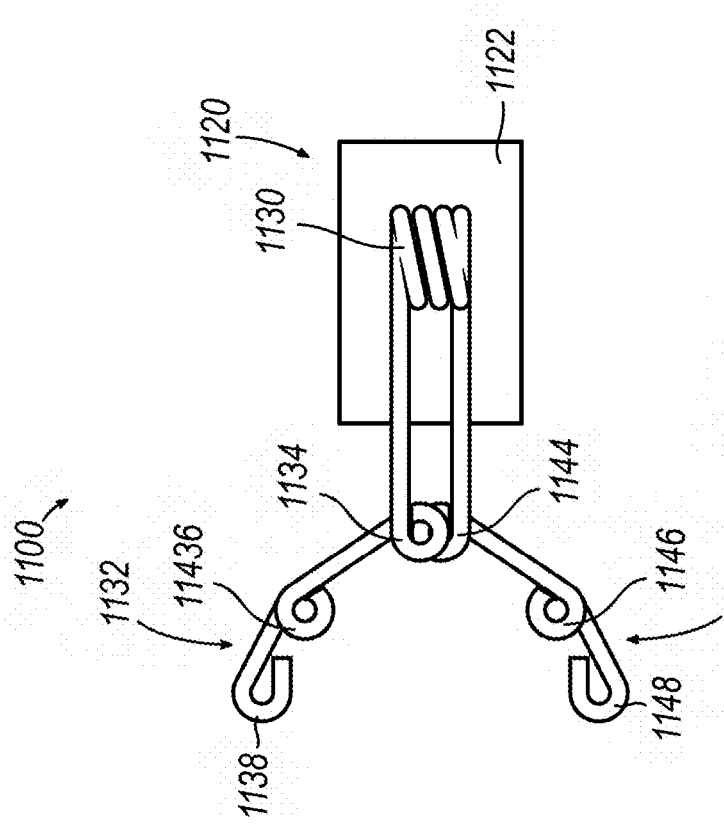
FIG. 12 depicts a top plan view of still another exemplary alternative marker for use with the marker delivery device of FIG. 2.

F. Exemplary Biopsy Site Marker with Anchors Having a Multi-Spring Configuration FIGS. 12 and 13 show an exemplary marker (1100) that is generally configured to anchor to tissue using anchors aligned along multiple planes to limit migration of marker (1100) relative to an initial placement in tissue. As with marker (100) described above, marker (1100) of the present example includes a carrier (1120) and a marker element (1112). As with carrier (120) described above, carrier (1120) of the present example generally includes a bioabsorbable marker material (1122). Thus, carrier (1120) is generally configured for absorption into a patient after placement of marker (1100) within a biopsy cavity such as biopsy cavity (10) described above. Carrier (1120) of the present example defines a generally cylindrical shape, although a variety of other shapes may be used. As similarly described above, some examples of carrier (1120) may include a plurality of microbubbles to enhance visualization of carrier (1120) under ultrasound.

Marker material (1122) of the present example comprise a hydrogel or other suitable materials. Hydrogel materials are generally configured to absorb into a patient's tissue over time. Thus, marker material (1122) is generally non-permanent. Additionally, hydrogel is generally configured to expand or swell when placed within tissue. As will be described in greater detail below, hydrogel may be dehydrated and/or cured prior to being deployed at a biopsy site or within a biopsy cavity. Once the hydrogel contacts tissue, the hydrogel may absorb moisture from the tissue and expand or swell as the moisture in the hydrogel increases. In some examples, the hydrogel may also be manipulated during dehydration and/or curing to control expansion of the hydrogel in accordance with various expansion profiles (e.g., limit longitudinal expansion, limit transverse expansion, and/or etc.). Although maker material (1122) is described herein as being hydrogel, it should be understood that in other examples marker material (1122) may comprise other suitable materials or include various combinations of suitable materials with or without hydrogel.

Marker element (1112) includes a primary coil (1130) and a plurality of anchors (1132, 1142) (alternatively referred to as "outriggers") extending outwardly from primary coil (1130). In the present example, primary coil (1130) is disposed entirely within carrier (1120). Primary coil (1130) is defined by one or more wire coils. Generally, the combination of the one or more wire coils forming primary coil (1130) are configured to provide a distinctive pattern to enhance visualization under x-ray and/or ultrasound visualization. Although primary coil (1130) is shown as having a particular orientation within carrier (1120) in the present example, it should be understood that primary coil (1130) may have a variety of alternative orientations in other examples.

Each anchor (1132, 1142) extends distally away from primary coil (1130) to protrude from a portion of carrier (1120). Each anchor (1132, 1142) includes a corresponding first spring (1134, 1144), second spring (1136, 1146), and secondary coil (1138, 1148). Each secondary coil (1138, 1148) is generally configured as one or more wire loops and is configured to promote tissue in-growth to provide enhanced anchoring of marker (1100). Each first spring (1134, 1144) and second spring (1136, 1146) is positioned along a length of each anchor (1132, 1142) between primary coil (1130) and a respective secondary coil (1138, 1148). As will be described in greater detail below, each of first spring (1134, 1144) and second spring (1136, 1146) are configured to bias a respective secondary coil (1138, 1148) outwardly and into tissue. As such, each first spring (1134, 1144) and second spring (1136, 1146) is positioned along the length of each anchor (1132, 1142) outside of carrier (1120).

Although anchors (1132, 1142) of the present example are shown as being substantially similar to each other, it should be understood that in other examples, anchors (1132, 1142) may have variation in structure. For instance, in some examples, one or more anchors (1132, 1142) may include additional springs, multiple coils, and/or different geometric profiles. Additionally, in some examples, anchors (1132, 1142) may be of varying lengths with one anchor (1132, 1142) being longer or shorter than one or more other anchors (1132, 1142). Various suitable combinations of such features will be apparent to those of ordinary skill in the art in view of the teachings herein.

The present example includes a first anchor (1132) and a second anchor (1142) extending distally from carrier (1120). As best shown in FIG. 13, first anchor (1132) and second anchor (1142) are laterally offset relative to each other. Such a lateral offset may be desirable to promote anchoring along multiple offset planes. For instance, first anchor (1132) in the present example is configured to provide anchoring along one plane, while second anchor (1142) is configured to provide anchoring along another plane laterally offset from the plane associated with first anchor (1132).

In an exemplary use, marker (1100) may initially be disposed in a tubular structure similar to outer cannula (162) of marker delivery device (150) for deployment at a biopsy site. To facilitate confinement within the tubular structure, anchors (1132, 1142) may bend about first springs (1134, 1144) and/or second springs (1136, 1146) to conform to the inner diameter of the tubular structure.

During deployment of marker (1100), marker (1100) may be ejected from the tubular structure as similarly described above with respect to marker delivery device (150). Once marker (1100) is released from the tubular structure, the resilient bias of springs (1134, 1136, 1144, 1146) may cause anchors (1132, 1142) to expand, thereby increasing the lateral profile or span of marker (1100). As a result, each secondary coil (1138, 1148) of each anchor (1132, 1142) may be forced into adjacent tissue to anchor marker (1100) at the biopsy site. Overtime, some tissue in-growth may occur with respect to each secondary coil (1138, 1148) further increasing anchoring of marker (1100) over time.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy site marker, comprising: a carrier; and a marker element including a primary coil, a first anchor and a second anchor, the primary coil being disposed within the carrier, at least a portion of the first anchor and the second anchor extending laterally and outwardly away from the primary coil and from opposite sides of the carrier, the first anchor and second anchor being configured to move relative to the primary coil to engage tissue at a biopsy site.

Example 2

The marker of Example 1, the first anchor and the second anchor extending laterally from the primary coil at an angle relative to a longitudinal axis defined by the carrier.

Example 3

The marker of Examples 1 or 2, the carrier including a hydrogel marker material.

Example 4

The marker of Example 3, the hydrogel marker material being configured to expand in the presence of moisture, the first anchor and second anchor being configured to respond to expansion of the hydrogel marker material to increase engagement of the first anchor and the second anchor with tissue.

Example 5

The marker of any one or more of Examples 1 through 4, the marker element further including a third anchor, the third anchor extending distally from the primary coil, a portion of the third anchor being disposed outside of the carrier.

Example 6

The marker of Example 5, the third anchor including one or more barbs, the one or more barbs being configured to penetrate and catch tissue.

Example 7

The marker of Example 6, the first anchor and the second anchor each including a secondary coil, the secondary coil being disposed on an outer end of each of the first anchor and the second anchor.

Example 8

The marker of any one or more of Examples 1 through 7, the primary coil being resiliently biased to drive the first anchor and the second anchor toward a predetermined position.

Example 9

The marker of Example 8, the predetermined position of the first anchor and the second anchor being disposed distally of an initial position defined by the first anchor and the second anchor.

Example 10

The marker of Example 9, the marker being configured for deployment from a cannula when the first anchor and the second anchor are disposed in the initial position.

Example 11

The marker of any one or more of Examples 1 through 11, the first anchor or the second anchor defining a spring disposed outside of the carrier.

Example 12

The marker of Example 11, the spring being configured to drive a portion of the first anchor or the second anchor into tissue.

Example 13

The marker of any one or more of Examples 1 through 12, the first anchor and the second anchor being connected to the primary coil at a first position and a second position, respectively, the first position being laterally offset relative to the second position.

Example 14

The marker of any one or more of Examples 1 through 13, the first anchor and the second anchor including a shape-memory alloy, the first anchor and the second anchor being configured to engage tissue when exposed to heat thereby activating a shape-memory property of the shape-memory alloy.

Example 15

The marker of Example 14, the first anchor and the second anchor being configured to form a predetermined curve when exposed to heat.

Example 16

A biopsy site marker, the biopsy site marker comprising: a carrier, the carrier having a first element and a second element; and a marker element extending between the first element and the second element of the carrier, the marker element having a resilient portion, the resilient portion being configured to transition the marker element between a pre-deployment state and a deployment state, the resilient portion being further configured to move the second element of the carrier relative to the first element when transitioning the marker element from between the pre-deployment state and the deployment state.

Example 17

The biopsy site marker of Example 16, the resilient portion including a spring.

Example 18

The biopsy site marker of Examples 16 or 17, the resilient portion being configured to move the second element of the carrier about 90° relative to the first element of the carrier.

Example 19

The biopsy site marker of any one or more of Examples 16 through 18, the marker element further including a first coil and a second coil, the first coil and the second coil being disposed on opposing ends of the marker element, the first coil being disposed within the first element of the carrier, the second coil being disposed within the second element of the carrier.

Example 20

A biopsy site marker, the biopsy site marker comprising: a carrier; and a marker element, the marker element including a braided portion disposed within the carrier and a plurality of anchor portions extending outside of the carrier from the braided portion.

Example 21

The biopsy site marker of Example 20, each anchor portion of the plurality of anchor portions being configured to move from each adjacent anchor portion to anchor the marker to tissue.

Example 22

The biopsy site marker of Examples 20 or 22, the carrier including a hydrogel marker material configured to expand in the presence of moisture, the hydrogel marker material being configured to drive movement of the plurality of anchor portions via expansion of the hydrogel marker material in the presence of moisture.

Example 23

A biopsy site marker, the biopsy site marker comprising: a carrier; and a marker element, the marker element including a body defining a coil shape, a first anchor, and a second anchor, the body being at least partially disposed within the carrier, the first anchor including a first spring and a second spring disposed between the body and an outer end of the first anchor, the second anchor including a third spring and a fourth spring disposed between the body and an outer end of the second anchor.

Example 24

The biopsy site marker of Example 23, the first anchor including a secondary coil disposed on the outer end of the first anchor, the second anchor including a secondary coil disposed on the outer end of the second anchor.

Example 25

The biopsy site marker of Examples 23 or 24, the first spring, the second spring, the third spring, and the fourth spring being configured to increase the span of the biopsy site marker across a lateral dimension.

Example 26

The biopsy site marker of any one or more of Examples 23 through 24, the marker element further including a third anchor and a fourth anchor, the first anchor and the second anchor extending distally from the body, the third anchor and the fourth anchor extending proximally from the body.

Example 27

The biopsy site marker of Example 26, the third anchor including a fifth spring disposed between the body and an outer end of the third anchor, the fourth anchor including a sixth spring disposed between the body and an outer end of the fourth anchor.

Example 28

The biopsy site marker of Example 26, the third anchor including a fifth spring and a sixth spring disposed between the body and an outer end of the third anchor, the fourth anchor including a seventh spring and an eighth spring disposed between the body and an outer end of the fourth anchor.

V. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy site marker, comprising:
a carrier including a hydrogel marker material; and
a marker element including a primary coil, a first anchor and a second anchor, the primary coil being disposed within the carrier, at least a portion of the first anchor and the second anchor extending laterally and outwardly from the primary coil and from opposite sides of the carrier, the first anchor and second anchor being configured to move relative to the primary coil to engage tissue at a biopsy site, the first anchor and the second anchor extending laterally from the primary coil at an angle relative to a longitudinal axis defined by the carrier.

2. The marker of claim 1, the hydrogel marker material being configured to expand in the presence of moisture, the first anchor and second anchor being configured to respond to expansion of the hydrogel marker material to increase engagement of the first anchor and the second anchor with tissue.

3. The marker of claim 1, the marker element further including a third anchor, the third anchor extending distally from the primary coil, a portion of the third anchor being disposed outside of the carrier.

4. The marker of claim 3, the third anchor including one or more barbs, the one or more barbs being configured to penetrate and catch tissue.

5. The marker of claim 4, the first anchor and the second anchor each including a secondary coil, the secondary coil being disposed on an outer end of each of the first anchor and the second anchor.

6. The marker of claim 1, the primary coil being resiliently biased to drive the first anchor and the second anchor toward a predetermined position.

7. The marker of claim 6, the predetermined position of the first anchor and the second anchor being disposed distally of an initial position defined by the first anchor and the second anchor.

8. The marker of claim 7, the marker being configured for deployment from a cannula when the first anchor and the second anchor are disposed in the initial position.

9. The marker of claim 1, the first anchor or the second anchor defining a spring disposed outside of the carrier.

10. The marker of claim 9, the spring being configured to drive a portion of the first anchor or the second anchor into tissue.

11. The marker of claim 1, the first anchor and the second anchor being connected to the primary coil at a first position and a second position, respectively, the first position being laterally offset relative to the second position.

12. The marker of claim 1, the first anchor and the second anchor including a shape-memory alloy, the first anchor and the second anchor being configured to engage tissue when exposed to heat thereby activating a shape-memory property of the shape-memory alloy.

13. The marker of claim 12, the first anchor and the second anchor being configured to form a predetermined curve when exposed to heat.

14. A biopsy site marker, comprising:
a carrier; and
a marker element including a primary coil, a first anchor and a second anchor, the primary coil being enclosed within the carrier, at least a portion of the first anchor and the second anchor extending along a same direction and outwardly away from the primary coil and from opposite sides of the carrier, the first anchor and second anchor being configured to move relative to the primary coil to engage tissue at a biopsy site, the first anchor and the second anchor extending laterally from the primary coil at an angle relative to a longitudinal axis defined by the carrier.

15. The marker of claim 14, the carrier including a hydrogel marker material.

16. The marker of claim 15, the hydrogel marker material being configured to expand in the presence of moisture, the first anchor and second anchor being configured to respond to expansion of the hydrogel marker material to increase engagement of the first anchor and the second anchor with tissue.

* * * * *